United States Patent [19]

Masuda et al.

[11] Patent Number: 4,968,613
[45] Date of Patent: Nov. 6, 1990

[54] LUCIFERASE GENE AND NOVEL RECOMBINANT DNA AS WELL AS A METHOD OF PRODUCING LUCIFERASE

[75] Inventors: Tsutomu Masuda, Needham, Mass.; Hiroki Tatsumi, Noda; Eiichi Nakano, Iwatsuki, both of Japan

[73] Assignee: Kikkoman Corporation, Noda, Japan

[21] Appl. No.: 224,445

[22] Filed: Jul. 26, 1988

[30] Foreign Application Priority Data

Jul. 29, 1987 [JP] Japan ................................ 62-187724
Jul. 29, 1987 [JP] Japan ................................ 62-187725
Aug. 20, 1987 [JP] Japan ................................ 62-205194

[51] Int. Cl.$^5$ ..................... C12N 15/00; C12N 7/00; C12N 15/52
[52] U.S. Cl. .................................. 435/172.3; 435/189; 435/320; 536/27; 935/14; 935/60; 935/29
[58] Field of Search ............... 435/68, 70, 235, 172.3, 435/320, 849, 253, 320, 272, 189, 69.1; 536/27; 935/14, 60, 29

[56] References Cited

U.S. PATENT DOCUMENTS 4,581,335 4/1986 Baldwin.

FOREIGN PATENT DOCUMENTS

WO87/03304 6/1987 PCT Int'l Appl..

OTHER PUBLICATIONS de Wet, J. R. et al., 1987, Mol. Cell. Biol., 7(2), 725–737.
Maniatis, T. et al., 1982, Molecular Cloning, A Laboratory Manual, Cold Spring Harbor Lab., pp. 224–228.
DeWet, J. R. et al., Proc. Natl. Acad. Sci. U.S.A., vol. 82, pp. 7870–7873; Dec. 1985.
DeLong, E. F. et al., Gene, vol. 54, No. 2-3, pp. 203–210, 1987.
Masuda, T. et al., Gene, vol. 77, pp. 265–270, 1989.
Chemical Abstracts, vol. 110, No. 13, p. 174, Abstract No. 109122g, Mar. 27, 1989.
Chem. Abs., 69(15):59203w, (1968).
Chem. Abs., 110(13):109122g, (1989).
Methods Enzymol, (1986), 133, (Biolumin. Chemilumin., Pt. B), pp. 3–14.
Tanpakushitsu, Kasusan, Kozo (Protein, Nucleic Acids and Enzymes), vol. 32, No. 10 (1987), pp. 1234–1249.
Shimomura et al., (1977), Proc. Natl. Acad. Sci., 74:2799–2802.
Kricka et al., (1982), Arch. Biochem. Biophys., 217:674–681.
Fukushi et al., (1982), Biomedical Res., 3:534–540.
Wienhausen et al., (1985), Photochem. Photobiol., 42:609–611.
Masuda et al., (1986), Agric. Biol. Chem., 50:271–279.
Ritao, Dec. 04, 1986, Abstract of 61/274683.
WO 88/00617

*Primary Examiner*—Robin L. Teskin
*Assistant Examiner*—Michelle S. Marks
*Attorney, Agent, or Firm*—Banner, Birch, McKie & Beckett

[57] ABSTRACT

A luciferase gene isolated from *Luciola cruciata* (Japanese firefly) coding for an amino acid sequence shown in FIG. 4 and a novel recombinant DNA characterized by incorporating a gene coding for luciferase into a vector DNA are disclosed. There is also disclosed a method of producing luciferase which comprises culturing in a medium a microorganism containing a recombinant DNA having inserted a gene coding for luciferase in a vector DNA and belonging to the genus Escherichia capable of producing luciferase and collecting luciferase from the culture.

10 Claims, 6 Drawing Sheets

```
         10         20         30         40         50         60
ATGGAAAACA TGGAAAACGA TGAAAATATT GTAGTTGGAC CTAAACCGTT TTACCCTATC
         70         80         90        100        110        120
GAAGAGGGAT CTGCTGGAAC ACAATTACGC AAATACATGG AGCGATATGC AAAACTTGGC
        130        140        150        160        170        180
GCAATTGCTT TTACAAATGC AGTTACTGGT GTTGATTATT CTTACGCCGA ATACTGGAAG
        190        200        210        220        230        240
AAATCATGTT GTCTAGGAAA AGCTTTGCAA AATTATGGTT TGGTTGTTGA TGGCAGAATT
        250        260        270        280        290        300
GCGTTATGCA GTGAAAACTG TGAAGAATTT TTTATTCCTG TAATAGCCGG ACTGTTTATA
        310        320        330        340        350        360
GGTGTAGGTG TTGCACCCAC TAATGAGATT TACACTTTAC GTGAACTGGT TCACAGTTTA
        370        380        390        400        410        420
GGTATCTCTA AACCAACAAT TGTATTTAGT TCTAAAAAAG GCTTAGATAA AGTTATAACA
        430        440        450        460        470        480
GTACAGAAAA CAGTAACTAC TATTAAAACC ATTGTTATAC TAGATAGCAA AGTTGATTAT
        490        500        510        520        530        540
CGAGGATATC AATGTCTGGA CACCTTTATA AAAAGAAACA CTCCACCAGG TTTTCAAGCA
        550        560        570        580        590        600
TCCAGTTTCA AAACTGTGGA AGTTGACCGT AAAGAACAAG TTGCTCTTAT AATGAACTCT
        610        620        630        640        650        660
TCGGGTTCTA CCGGTTTGCC AAAAGGCGTA CAACTTACTC ACGAAAATAC AGTCACTAGA
        670        680        690        700        710        720
TTTTCTCATG CTAGAGATCC GATTTATGGT AACCAAGTTT CACCAGGCAC CGCTGTTTTA
        730        740        750        760        770        780
ACTGTCGTTC CATTCCATCA TGGTTTTGGT ATGTTCACTA CTCTAGGGTA TTTAATTTGT
        790        800        810        820        830        840
GGTTTTCGTG TTGTAATGTT AACAAAATTC GATGAAGAAA CATTTTTAAA AACTCTACAA
```

FIG. 3-(2)

```
     850        860        870        880        890        900
GATTATAAAT GTACAAGTGT TATTCTTGTA CCGACCTTGT TTGCAATTCT CAACAAAAGT
     910        920        930        940        950        960
GAATTACTCA ATAAATACGA TTTGTCAAAT TTAGTTGAGA TTGCATCTGG CGGAGCACCT
     970        980        990       1000       1010       1020
TTATCAAAAG AAGTTGGTGA AGCTGTTGCT AGACGCTTTA ATCTTCCCGG TGTTCGTCAA
    1030       1040       1050       1060       1070       1080
GGTTATGGTT TAACAGAAAC AACATCTGCC ATTATTATTA CACCAGAAGG AGACGATAAA
    1090       1100       1110       1120       1130       1140
CCAGGAGCTT CTGGAAAAGT CGTGCCGTTG TTTAAAGCAA AAGTTATTGA TCTTGATACC
    1150       1160       1170       1180       1190       1200
AAAAAATCTT TAGGTCCTAA CAGACGTGGA GAAGTTTGTG TTAAAGGACC TATGCTTATG
    1210       1220       1230       1240       1250       1260
AAAGGTTATG TAAATAATCC AGAAGCAACA AAAGAACTTA TTGACGAAGA AGGTTGGCTG
    1270       1280       1290       1300       1310       1320
CACACCGGAG ATATTGGATA TTATGATGAA GAAAAACATT TCTTTATTGT CGATCGTTTG
    1330       1340       1350       1360       1370       1380
AAGTCTTTAA TCAAATACAA AGGATACCAA GTACCACCTG CCGAATTAGA ATCCGTTCTT
    1390       1400       1410       1420       1430       1440
TTGCAACATC CATCTATCTT TGATGCTGGT GTTGCCGGCG TTCCTGATCC TGTAGCTGGC
    1450       1460       1470       1480       1490       1500
GAGCTTCCAG GAGCCGTTGT TGTACTGGAA AGCGGAAAAA ATATGACCGA AAAAGAAGTA
    1510       1520       1530       1540       1550       1560
ATGGATTATG TTGCAAGTCA AGTTTCAAAT GCAAAACGTT TACGTGGTGG TGTTCGTTTT
    1570       1580       1590       1600       1610       1620
GTGGATGAAG TACCTAAAGG TCTTACTGGA AAAATTGACG GCAGAGCAAT TAGAGAAATC
    1630       1640
CTTAAGAAAC CAGTTGCTAA GATG
```

FIG. 4-(1)

| | | | | | | | | | 10 | | | | | | | | | | 20 |
|---|---|---|---|---|---|---|---|---|---|---|---|---|---|---|---|---|---|---|---|
| Met | Glu | Asn | Met | Glu | Asn | Asp | Glu | Asn | Ile | Val | Val | Gly | Pro | Lys | Pro | Phe | Tyr | Pro | Ile |
| | | | | | | | | | 30 | | | | | | | | | | 40 |
| Glu | Glu | Gly | Ser | Ala | Gly | Thr | Gln | Leu | Arg | Lys | Tyr | Met | Glu | Arg | Tyr | Ala | Lys | Leu | Gly |
| | | | | | | | | | 50 | | | | | | | | | | 60 |
| Ala | Ile | Ala | Phe | Thr | Asn | Ala | Val | Thr | Gly | Val | Asp | Tyr | Ser | Tyr | Ala | Glu | Tyr | Leu | Glu |
| | | | | | | | | | 70 | | | | | | | | | | 80 |
| Lys | Ser | Cys | Cys | Leu | Gly | Lys | Ala | Leu | Gln | Asn | Tyr | Gly | Leu | Val | Val | Asp | Gly | Arg | Ile |
| | | | | | | | | | 90 | | | | | | | | | | 100 |
| Ala | Leu | Cys | Ser | Glu | Asn | Cys | Gln | Glu | Phe | Ile | Pro | Val | Ile | Ala | Gly | Leu | Phe | | Ile |
| | | | | | | | | | 110 | | | | | | | | | | 120 |
| Gly | Val | Gly | Val | Ala | Pro | Thr | Asn | Glu | Ile | Tyr | Thr | Leu | Arg | Glu | Leu | Val | His | Ser | Leu |
| | | | | | | | | | 130 | | | | | | | | | | 140 |
| Gly | Ile | Ser | Lys | Pro | Thr | Val | Thr | Ile | Val | Phe | Ser | Ser | Lys | Lys | Gly | Leu | Asp | Lys | Thr |
| | | | | | | | | | 150 | | | | | | | | | | 160 |
| Val | Gln | Lys | Thr | Gln | Cys | Leu | Asp | Thr | Phe | Ile | Lys | Val | Ile | Leu | Leu | Asp | Ser | Val | Tyr |
| | | | | | | | | | 170 | | | | | | | | | | 180 |
| Arg | Gly | Tyr | Gln | Cys | Leu | Asp | Thr | Phe | Ile | Lys | Arg | Asn | Thr | Pro | Pro | Gly | Phe | Gln | Ala |
| | | | | | | | | | 190 | | | | | | | | | | 200 |
| Ser | Ser | Phe | Lys | Thr | Val | Glu | Val | Asp | Arg | Lys | Glu | Gln | Val | Ala | Leu | Ile | Met | Asn | Ser |
| | | | | | | | | | 210 | | | | | | | | | | 220 |
| Ser | Gly | Ser | Thr | Gly | Leu | Pro | Lys | Gly | Val | Gln | Leu | Thr | His | Glu | Asn | Thr | Val | Thr | Arg |
| | | | | | | | | | 230 | | | | | | | | | | 240 |
| Phe | Ser | His | Ala | Arg | Asp | Pro | Ile | Tyr | Asn | Gln | Val | Ser | Pro | Gly | Thr | Ala | Val | Leu | Leu |
| | | | | | | | | | 250 | | | | | | | | | | 260 |
| Thr | Val | Val | Pro | Phe | His | His | Gly | Phe | Gly | Met | Phe | Thr | Thr | Leu | Gly | Tyr | Leu | Ile | Cys |
| | | | | | | | | | 270 | | | | | | | | | | 280 |
| Gly | Phe | Arg | Val | Val | Met | Leu | Thr | Lys | Phe | Asp | Glu | Glu | Thr | Phe | Leu | Lys | Thr | Leu | Gln |

FIG. 4-(2)

```
                                        290                    300
Asp Tyr Lys Cys Thr Ser Val Ile Leu Val Pro Thr Leu Phe Ala Ile Leu Asn Lys Ser
                                        310                    320
Glu Leu Leu Asn Lys Tyr Asp Ser Leu Asn Leu Val Glu Ala Ile Ser Gly Gly Ala Pro
                                        330                    340
Leu Ser Lys Glu Val Gly Ala Val Ala Arg Arg Phe Asn Leu Pro Gly Val Arg Val Gln
                                        350                    360
Gly Tyr Gly Leu Thr Glu Thr Thr Ser Ala Ile Ile Ile Thr Pro Gly Gly Val Asp Lys
                                        370                    380
Pro Gly Ala Ser Gly Lys Val Val Pro Leu Phe Lys Ala Lys Val Ile Asp Leu Asp Thr
                                        390                    400
Lys Lys Ser Leu Gly Pro Asn Arg Arg Gly Glu Val Cys Val Lys Gly Pro Met Leu Met
                                        410                    420
Lys Gly Tyr Val Asn Asn Pro Glu Ala Thr Lys Glu Leu Ile Asp Glu Glu Gly Trp Leu
                                        430                    440
His Thr Gly Asp Ile Gly Tyr Tyr Asp Glu Glu Lys His Phe Phe Ile Val Asp Arg Leu
                                        450                    460
Lys Ser Leu Ile Lys Tyr Lys Gly Tyr Gln Val Pro Pro Ala Glu Leu Glu Ser Val Leu
                                        470                    480
Leu Gln His Pro Ser Ile Phe Asp Ala Gly Val Ala Gly Val Pro Asp Pro Val Ala Gly
                                        490                    500
Glu Leu Pro Gly Ala Val Val Val Leu Glu Ser Gly Lys Asn Met Thr Glu Lys Glu Val
                                        510                    520
Met Asp Tyr Val Ala Ser Gln Val Ser Asn Ala Lys Arg Leu Arg Gly Gly Val Arg Phe
                                        530                    540
Val Asp Glu Val Pro Lys Gly Leu Thr Gly Lys Ile Asp Gly Arg Ala Ile Arg Glu Ile

Leu Lys Lys Pro Val Ala Lys Met
```

LUCIFERASE GENE AND NOVEL RECOMBINANT DNA AS WELL AS A METHOD OF PRODUCING LUCIFERASE

BACKGROUND OF THE INVENTION

1. Field of the Invention

The present invention relates to a luciferase gene derived from *Luciola cruciata* and a novel recombinant DNA having inserted therein the luciferase gene as well as a method of producing luciferase.

2. Discussion of Related Art

Luciferase from fireflies belonging to the genus Luciola is obtained simply by isolating and purifying from the collected fireflies belonging to the genus Luciola [Proc. Natl. Acad. Sci., 74 (7), 2799-2802 (1977)].

Luciferase is an enzyme which is extremely useful as an enzyme, e.g., for ATP assay.

However, the luciferase described above is derived from insects and hence, for producing luciferase, fireflies belonging to the genus Luciola must be collected from the natural world or such fireflies must be cultivated and luciferase should be isolated and refined from the fireflies so that much time and labors are required for the production.

As a result of various investigations to solve the foregoing problems, the present inventors have found that by obtaining a recombinant DNA having incorporated DNA containing a gene coding for luciferase into a vector DNA and culturing in a medium a luciferase-producing microorganism belonging to the genus Escherichia containing the recombinant DNA, luciferase can be efficiently produced in a short period of time, and the like. Also as a result of further investigations on luciferase gene derived from *Luciola cruciata*, the present inventors have succeeded in isolating a luciferase gene derived from *Luciola cruciata* and determining its structure, for the first time and, have thus accomplished the present invention.

SUMMARY OF THE INVENTION

That is, a first aspect of the present invention lies in a luciferase gene coding for an amino acid sequence shown in FIG. 4.

A second aspect of the present invention resides in a novel recombinant DNA characterized by incorporating a gene coding for luciferase into a vector DNA.

A third aspect of the present invention resides in a method of producing luciferase which comprises culturing in a medium a microorganism containing a recombinant DNA having inserted a gene coding for luciferase in a vector DNA and belonging to the genus Escherichia capable of producing luciferase and collecting luciferase from the culture.

BRIEF DESCRIPTION OF THE DRAWINGS

FIGS. 3-(1)-3-(2) shows a base sequence of the luciferase gene in accordance with the present invention.

FIGS. 4-(1)-4-(2) shows an amino acid sequence of polypeptide translated from the luciferase gene of the present invention.

DETAILED DESCRIPTION OF THE PREFERRED EMBODIMENTS

Figure 1:
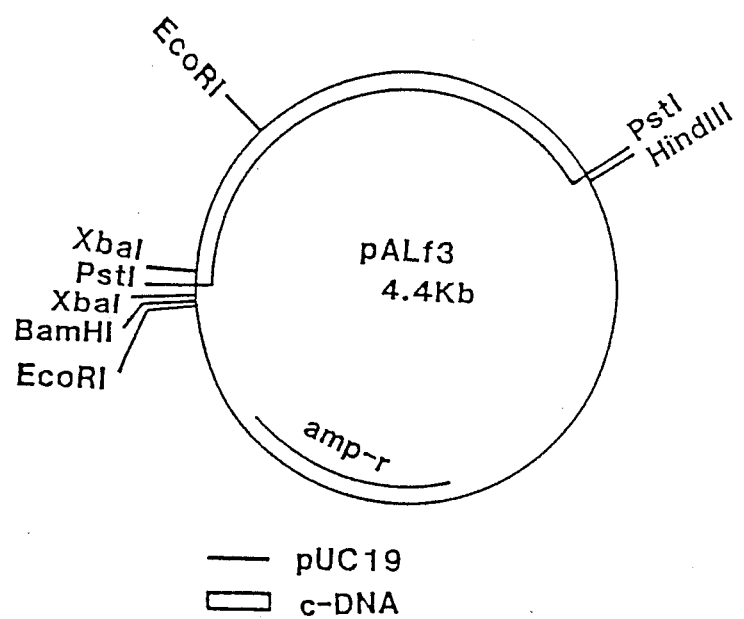
FIG. 1 shows a cleavage map of recombinant plasmid pALf3 DNA with restriction enzymes.

It has been hitherto attempted to isolate luciferase from *Luciola cruciata*; however, the enzyme per se is unstable and such causes a problem that the enzyme could be provided for practical use only with difficulty. Luciferase obtained in accordance with the present invention is advantageous in that it is stable and its activity is also high.

Hereafter the present invention will be described in detail.

In survey of DNA containing a gene coding for luciferase of *Luciola cruciata*, DNA containing a gene coding for luciferase derived from *Photinus pyralis* which is one of fireflies is used as a probe. Therefore, preparation of the DNA is described below.

Preparation of m-RNA from the tail of *Photinus pyralis* which is one of fireflies can be effected by methods described in, for example, Molecular Cloning, page 196, Cold Spring Harbor Laboratory (1982), Haruo Ozeki and Reiro Shimura, BUNSHI IDENGAKU JIKKENHO (Experimental Molecular Genetics), pages 66-67 (1983), etc.

Concentration of m-RNA coding for luciferase from the obtained m-RNA can be performed by a method described in, for example, Biomedical Research, 3, 534-540 (1982) or the like.

In this case, anti-luciferase serum to luciferase is used. This serum can be obtained by, for example, Yuichi Yamamura, MEN-EKI KAGAKU (Immunochemistry), pages 43-50 (1973), etc.

Synthesis of c-DNA from m-RNA coding for luciferase can be performed by methods described in, for example, Mol. Cell Biol., 2, 161 (1982) and Gene, 25, 263 (1983).

Then, the thus obtained c-DNA is incorporated into, for example, plasmid pMCE10 DNA [plasmid prepared using plasmid pKN 305 [plasmid having a promoter of *Escherichia coli* tryptophane operator described in Agr. Biol. Chem., 50, 271 (1986)] and plasmid pMC 1843 [plasmid containing *Escherichia coli* β-galactosidase structural gene described in Methods in Enzymology, 100, 293-308 (1983)]], etc. to obtain various recombinant plasmid DNAs. Using these DNAs, transformation of *Escherichia coli* (*E. coli*) DH1 (ATCC 33849), *Escherichia coli* (*E. coli*) HB 101 (ATCC 33694), etc. is effected by the method of Hanahan [DNA Cloning, 1, 109-135 (1985)] to obtain various transformants.

The recombinant plasmid DNAs possessed by the thus obtained transformants are plasmids wherein c-DNA has been incorporated in the middle of *Escherichia coli* β-galactosidase structural gene. A peptide encoded by c-DNA is expressed as a protein fused with β-galactosidase.

In order to detect c-DNA coding for luciferase from the various transformants described above, the transformants are cultured thereby to express cell protein. By determining if any protein crossing over anti-luciferase serum is present, the detection can be made. Methods descried in, for example, Agric. Biol. Chem., 50, 271 (1986) and Anal. Biochem., 112, 195 (1981), etc. can be used for the detection.

Next, after labeling c-DNA of incomplete luciferase with $^{32}P$ by the nick translation method [Molecular Cloning, pages 109-112, Cold Spring Harbor Laboratory (1982) and J. Mol. Biol., 113, 237-251 (1977)], using the colony hybridization method [Protein, Nucleic Acid & Enzyme, 26, 575–579 (1981)], an *Escherichia coli* strain having plasmid DNA containing *Photinus pyralis* luciferase c-DNA of 1.8 Kb can be obtained from a *Photinus pyralis*-derived c-DNA library prepared using plasmid pUC19 DNA (manufactured by Takara Shuzo Co., Ltd.) as a vector.

To obtain the purified plasmid DNA, there is used, for example, a method described in Proc. Natl. Acad. Sci., 62 1159–1166 (1969), etc.

To obtain DNA containing the gene coding for luciferase derived from *Photinus pyralis* from the thus obtained recombinant plasmid DNA, restriction enzymes, e.g., EcoR I and Cla I, are acted on the plasmid DNA at temperatures of 30° to 40° C., preferably at 37° C., for 1 to 24 hours, preferably 2 hours; the solution obtained after completion of the reaction is subjected to agarose gel electrophoresis [which is described in Molecular Cloning, page 150, Cold Spring Harbor Laboratory (1982)] to obtain DNA containing the gene coding for luciferase derived from *Photinus pyralis*.

Next, preparation of the luciferase gene and the like in accordance with the present invention are described below.

Firstly, source from which the gene coding for luciferase is derived may be any source and, mention may be made of, for example, *Luciola cruciata*, etc. Particularly preferred is the tail part of this firefly.

And preparation of m-RNA from the tail of the firefly and synthesis of c-DNA from m-RNA can be conducted, for example, in quite the same manner as in the preparation of m-RNA of *Photinus pyralis* and synthesis of c-DNA described above.

Then, the thus obtained c-DNA is incorporated into a vector DNA, for example, plasmid pUC 19 DNA (manufactured by Takara Shuzo Co., Ltd.), etc. to obtain various recombinant plasmid DNAs. Using these DNAs, transformation of *Escherichia coli* (*E. coli*) DH1 (ATCC 33849), *Escherichia coli* (*E. coli*) HB 101 (ATCC 33694), etc. is effected by the method of Hanahan [DNA Cloning, 1, 109–135 (1985)] to obtain various transformants.

Next, after labeling DNA containing the gene coding for luciferase derived from *Photinus pyralis* with $^{32}P$ by the nick translation method [Molecular Cloning, pages 109–112, Cold Spring Harbor Laboratory (1982) and J. Mol. Biol., 113, 237–251 (1977)], using the colony hybridization method [Protein, Nucleic Acid & Enzyme, 26, 575–579 (1981)], an *Escherichia coli* strain having plasmid DNA containing *Luciola cruciata* luciferase c-DNA of 2.0 Kb can be obtained from the gene library of *Luciola cruciata*-derived c-DNA.

To obtain the purified plasmid DNA, there is used, for example, a method described in Proc. Natl. Acad. Sci., 62 1159–1166 (1969), etc.

By acting on the purified plasmid DNA, for example, restriction enzyme Pst I (manufactured by Takara Shuzo Co., Ltd.) at a temperature of 30° C. or higher, preferably 37° C. in an enzyme concentration of 200 to 400 units/ml for 1 to 4 hours, preferably 4 hours to effect digestion, a DNA fragment mixture is obtained.

Isolation from the DNA fragment mixture described above of DNA containing the gene coding for luciferase derived from *Luciola cruciata* can be performed by quite the same manner as in the isolation of DNA containing the gene coding for luciferase derived from *Photinus pyralis*.

Next, by acting a restriction enzyme, e.g., Ssp I [manufactured by New England Biolab Co., Ltd.] on the plasmid DNA containing c-DNA encoding *Luciola cruciata* of 2.0 Kb in a conventional manner, DNA containing c-DNA coding for luciferase of 1.6 Kb is obtained. The DNA is incorporated into a vector DNA to give a novel recombinant DNA.

As the vector DNA described above, any vector DNA may be used. Mention may be made of, for example, plasmid vector DNA, bacteriophage vector DNA, etc. Specific examples are pUC 18 (manufactured by Takara Shuzo Co., Ltd.), pUC 19 (manufactured by Takara Shuzo Co., Ltd.), $\lambda cI857h80att\lambda sRI\lambda_3{}^0 sRI\lambda_2{}^0 - sRI\lambda_1{}^0$ (described in Japanese Patent Publication KOKOKU No. 61-37917), etc.

Using the thus obtained novel recombinant DNA, microorganism belonging to the genus Escherichia, for example, *Escherichia coli* JM 101 (ATCC 33876) or the like, is transformed by the method of Cohen et al. [J. Bac., 119, 1072–1074 (1974)] or transfected by the method described in Molecular Cloning, pages 256–268, Cold Spring Harbor Laboratory (1982)] to give luciferase-producing microorganism belonging to the genus Escherichia containing the novel recombinant DNA having inserted the luciferase-encoding gene into vector DNA.

To obtain a purified novel recombinant DNA from the thus obtained microorganism, there is used, for example, a method described in Proc. Natl. Acad. Sci., 62, 1159–1166 (1969), etc.

By acting on the purified novel recombinant DNA described above, for example, restriction enzyme Pst I (manufactured by Takara Shuzo Co., Ltd.) at a temperature of 30° C. or higher, preferably 37° C. in an enzyme concentration of 200 to 400 units/ml for 1 to 4 hours, preferably 4 hours to effect digestion, a DNA fragment mixture is obtained.

Isolation from the DNA fragment mixture described above of DNA containing the gene coding for luciferase derived from *Luciola cruciata* can be performed by quite the same manner as in the isolation of DNA containing the gene coding for luciferase derived from *Photinus pyralis*.

Next, the microorganism described above is cultured in a medium and luciferase is collected from the culture.

Any medium may be used as far as it is used for culture of microorganism belonging to the genus Escherichia. Mention may be made of, for example, 1% (W/V) of Tripton, 0.5% (W/V) of yeast extract, 0.5% (W/V) of NaCl and 1 mM of isopropyl-$\beta$-D-thiogalactoside, etc.

Temperature for the cultivation is between 30° and 40° C., preferably about 37° C. and a time period for the cultivation is, for example, 4 to 8 hours, preferably about 4 hours.

The cells are collected from the culture by centrifugation at 8,000 r.p.m. for about 10 minutes. The obtained cells are homogenized by the method described in, for example, Methods in Enzymology, 133, 3–14 (1986) to obtain a crude enzyme solution.

The crude enzyme solution may be usable as it is; if necessary and desired, the crude enzyme solution can be purified by fractionation with ammonium sulfate, hydrophobic chromatography, for example, using Butyl Toyo Pearl 650 C, etc., gel filtration using, e.g., Ultrogel AcA 34, etc. thereby to give purified luciferase.

Physicochemical properties of the thus obtained luciferase are quite the same as those described in Photochem. Photobiol., 42, 609–611 (1985).

As is clear from the foregoing description, according to the present invention, luciferase can be efficiently produced in an extremely short period of time by culturing the microorganism belonging to the genus Escherichia which contains the recombinant DNA having incorporated therein the luciferase gene of the present invention. Therefore, the present invention is extremely useful from an industrial point of view.

Hereafter the present invention will be described in more detail by referring to the examples below.

EXAMPLE

In Items 1 to 10 below, preparation of DNA containing a gene coding for luciferase of *Photinus pyralis* as one of fireflies (this DNA is used as a probe upon survey of DNA containing a gene coding for luciferase of *Luciola cruciata*) is described.

1. Preparation of m-RNA

Using a mortar and a pestle, 1 g of the dry tail (manufactured by Sigma Co., Ltd.) of *Photinus pyralis* as one of fireflies was thoroughly homogenized, to which 5 ml of dissolution buffer [20 mM Tris-hydrochloride buffer (pH 7.4)/10 mM NaCl/3 mM magnesium acetate/5% (W/V) sucrose/1.2 % (V/V) Triton X-100/10 mM vanadyl nucleoside complex (manufactured by New England Biolab Co., Ltd.)] was added. The mixture was further homogenized as in the manner described above to give a solution containing the homogenized tail of *Photinus pyralis*.

In a cup blender (manufactured by Nippon Seiki Seisakusho) was charged 5 ml of the thus obtained solution. After treating at 5,000 r.p.m. for 5 minutes, 12 ml of guanidine isothiocyanate solution (6M guanidine isothiocyanate/37.5 mM sodium citrate (pH 7.0)/0.75% (W/V) sodium N-lauroylsarcocine/0.15 M β-mercaptoethanol) was added to the system. The mixture was treated with the blender described above at 3,000 r.p.m. for 10 minutes. The resulting solution was filtered using a threefold gauze to give the filtrate. The filtrate was gently poured in layers onto 4 tubes for ultracentrifuging machine (manufactured by Hitachi Koki Co., Ltd.) in which 1.2 ml each of 5.7 M cesium chloride solution had previously be laid in layers. Using the ultracentrifuging machine (manufactured by Hitachi Koki Co., Ltd., SCP55H), centrifugation was performed at 30,000 r.p.m. for 16 hours to give precipitates.

The obtained precipitates were washed with chilled 70% (V/V) ethanol and suspended in 4 ml of 10 mM Tris buffer [10 mM Tris-hydrochloride (pH 7.4)/5 mM EDTA/1% sodium dodecyl sulfate]. A mixture of the same amount of n-butanol and chloroform in 1:4 (volume ratio) was added to the mixture to perform extraction. The extract was centrifuged at 3,000 r.p.m. for 10 minutes in a conventional manner to separate into the aqueous phase and the organic solvent phase. To the organic solvent phase was added 4 ml of 10 mM Tris buffer described above. The extraction and separation operations described above were repeated twice. To the aqueous phase obtained were added a 1/10 amount of sodium 3 M sodium acetate (pH 5.2) and a 2-fold amount of cold ethanol were added. After allowing to stand at a temperature of −20° C. for 2 hours, the mixture was centrifuged at 8,000 r.p.m. for 20 minutes in a conventional manner to precipitate RNA. The obtained RNA was dissolved in 4 ml of water. After the operation for precipitation with ethanol described above was carried out, the obtained RNA was dissolved in 1 ml of water to give 3.75 mg of RNA.

By repeating the foregoing operations again, 7 mg in total of RNA was prepared. To select m-RNA from the RNA, 7 mg of RNA was subjected to oligo (dT)-cellulose (manufactured by New England Biolab Co., Ltd.) column chromatography.

As the column, 2.5 ml of Terumo syringe (manufactured by Terumo Co., Ltd.) was used. After 0.5 g of resin was swollen with elution buffer [10 mM Tris-hydrochloride buffer (pH 7.6)/1 mM DETA/0.1% (W/V) sodium dodecylsulfate], the resin was packed in the column and equilibrated with binding buffer [10 mM Tris-hydrochloride (pH 7.6)/1 mM DETA/0.4 M NaCl/0.1% (W/V) sodium dodecylsulfate].

To 7 mg of RNA was added the same amount of buffer [10 mM Tris-hydrochloride (pH 7.6)/1 mM DETA/0.8 M NaCl/0.1% (W/V) sodium dodecylsulfate]. The mixture was heat-treated at a temperature of 65° C. for 10 minutes and then quenched in ice water. After subjecting to oligo(dT)-celluose column, the resin was washed with binding buffer to completely wash unbound r-RNA and t-RNA out. Further m-RNA was eluted with eluting buffer to give 40 µg of m-RNA.

2. Concentration of luciferase m-RNA

Sucrose density gradient of 10 to 25% (W/V) was prepared by charging 0.5 ml of 40% (W/V) sucrose solution [50 mM Tris-hydrochloride buffer (pH 7.5)/20 mM NaCl/1 mM EDTA/40% (W/V) sucrose] in a polyaroma tube for Rotar SW 41 manufactured by Beckmann Co., Ltd., laying 2.4 ml each of 25% (W/V), 20% (W/V), 15% (W/V) and 10% (W/V) of the sucrose solution in layers and allowing to stand the system at a temperature of 4° C. for 24 hours. To the sucrose density gradient, 30 µg of m-RNA was laid to form a layer. Using SW 41 Rotar manufactured by Beckmann Co., Ltd., centrifugation was conducted at 30,000 r.p.m. at a temperature of 18° C. for 18 hours in a conventional manner. After the centrifuging operation, 0.5 ml each was fractionated and m-RNA was recovered by the ethanol precipitation method and dissolved in 10 µl of water.

Next, protein encoded by m-RNA was examined, whereby the fraction concentrated on m-RNA of luciferase was identified. The fractionated RNA, 1 µl, 9 µl of rabbit reticular erythrocyte lysate (manufactured by Amersham Co., Ltd.) and 1 µl of [$^{35}$S] methionine (manufactured by Amersham Co., Ltd.) were mixed and reacted at a temperature of 30° C. for 30 minutes. To the reaction mixture was added 150 µl of NET buffer [150 mM NaCl/5 mM EDTA/0.02% (W/V) NaN$_3$/20 mM Tris-hydrochloride buffer (pH 7.4)/0.05% (W/V) Nonidet P-40 (manufactured by Besesda Research Laboratories Co., Ltd., surface active agent)] and, 1 µl of anti-luciferase serum (prepared as will be later described) was added to the mixture. After allowing to stand at a temperature of 20° C. for 30 hours, 10 mg of Protein A Sepharose (manufactured by Pharmacia Fine Chemicals Inc.) was added to the mixture. The resulting mixture was then centrifuged at 12,000 r.p.m. for a minute in a conventional manner to recover the resin.

The recovered resin was washed three times with 200 µl of NET buffer. To the resin was added 40 µl of sample buffer for SDS-PAGE [62.5 mM Tris-hydrochloride buffer (pH 6.8)/10% (V/V) glycerol/2% (W/V) sodium dodecylsulfate/5% (V/V) mercaptoethanol/0.02% (W/V) bromophenol blue]. The mixture was boiled at a temperature of 100° C. for 3 minutes and centrifuged at 12,000 r.p.m. for a minute in a conventional manner to recover the supernatant. The whole amount was applied onto 7.5% (W/V) sodium dodecylsulfate-polyocrylamide gel.

Gel electrophoresis was performed by the method of Laemmli [Nature, 227, 680 (1970)]. After the electrophoresis, the gel was immersed in 10% (V/V) acetic acid for 30 minutes to immobilize protein. Then, the gel was immersed in water for 30 minutes and further immersed in 1 M sodium salicylate solution for 30 minutes and then dried to give a dry gel. The dry gel was subjected to fluorography using an X ray film (manufactured by Fuji Photo Film Co., Ltd., RX).

From the foregoing operations, the band of luciferase protein was recognized on the X ray film only in the case of using RNA in the fraction in which luciferase m-RNA was present and, the fraction wherein luciferase m-RNA was concentrated could be identified.

3. Preparation of anti-serum

Rabbit anti-luciferase serum to purified luciferase was prepared by the following method.

Luciferase solution having a 3.2 mg/ml concentration [solution obtained by dissolving luciferase manufactured by Sigma Co., Ltd. in 0.5 M glycylglycine solution (pH 7.8)], 0.7 ml, was suspended in an equivalent amount of Freund's complete adjuvant. 2.24 mg of the suspension was administered to the palm of Japanese white rabbit weighing 2 kg as an antigen. After feeding for 2 weeks, the same amount of antigen as in the initial amount was intracutaneously administered to the back. After feeding for further one week, similar operation was performed. Further one week after feeding, whole blood was collected.

The obtained blood was allowed to stand at a temperature of 4° C. for 18 hours and centrifuged at 3,000 r.p.m. for 15 minutes in a conventional manner to give anti-luciferase serum as the supernatant.

4. Synthesis of c-DNA

Synthesis of c-DNA was carried out using a kit manufactured by Amersham Co., Ltd.

Using 2 µg of m-RNA obtained as described above, synthesis of c-DNA was carried out in accordance with the methods described in Mol. Cell Biol., 2, 161 (1982) and Gene, 25, 263 (1983). As a result, 300 ng of double stranded c-DNA was obtained.

This c-DNA, 150 ng, was dissolved in 7 µl of TE buffer [10 mM Tris-hydrochloride buffer (pH 7.5)/1 mM EDTA]. To the solution were added, respectively, 11 µl of a mixture [280 mM sodium cacodylate (pH 6.8)/60 mM Tris-hydrochloride buffer (pH 6.8)/2 mM cobalt chloride] and 3.8 µl of a tailing mixture [7.5 µl of 10 mM dithiothreitol/1 µl of 10 ng/ml poly(A)/2 µl of 5 mM dCTP/110 µl of water]. Further 29 units of terminal transferase (manufactured by Boehringer Mannheim AG) was added to the mixture. After reacting at a temperature of 30° C. for 10 minutes, 2.4 µl of 0.25 M EDTA and 2.4 µl of 10% (W/V) sodium dodecyl sulfate were added to the mixture to discontinue the reaction.

The solution which reaction had been discontinued was subjected to a treatment for removing protein using 25 µl of water-saturated phenol. Then, 25 µl of 4 M ammonium acetate and 100 µl of cold ethanol were added to the recovered aqueous phase, respectively. The mixture was allowed to stand at a temperature of −70° C. for 15 minutes and centrifuged at 12,000 r.p.m. for 10 minutes to recover c-DNA. c-DNA was dissolved in 10 µl of TE buffer to give a c-DNA solution.

As described above, 100 ng of c-DNA with the deoxycytidine tail was obtained.

5. Preparation of recombinant plasmid pMCE10 DNA used in vector

Plasmid pKN305 DNA prepared by the method described in T. Masuda et al., Agricultural Biological Chemistry, 50, 271–279 (1986) using *Escherichia coli* W3110 strain (ATCC 27325) and plasmid pBR 325 (manufactured by BRL Co.) and plasmid pBR 322 DNA (manufactured by Takara Shuzo Co., Ltd.) as well as pMC 1403-3 DNA (described in Japanese Patent Publication KOKAI No. 61-274683) were added by 1 µg each to 10 µl of a mixture [50 mM Tris-hydrochloride buffer (pH 7.5)/10 mM MgCl$_2$/100 mM NaCl/1 mM dithiothreitol]. Further, 2 units each of Hind III and Sal I (both manufactured by Takara Shuzo Co., Ltd.) were added to the mixture. By reacting at a temperature of 37° C. for an hour, a cleavage treatment was effected. Extraction with phenol and precipitation with ethanol were conducted in a conventional manner to give precipitates. The precipitates were dissolved in 10 µl of ligation buffer [20 mM MgCl$_2$/66 mM Tris-hydrochloride buffer (pH 7.6)/1 mM ATP/15 mM dithiothreitol] to give a solution. Further 1 unit of T4DNA ligase (manufactured by Takara Shuzo Co., Ltd.) was added thereto to perform ligation at a temperature of 20° C. for 4 hours. Then, using this reaction solution, *Escherichia coli* JM 101 (ATCC 33876) was transformed according to the transformation method described in [J. Bacteriology, 119, 1072–1074 (1974)]. By examination of chemical resistance (ampicillin resistance and tetracycline resistance) and $\beta$-galactosidase activity, a transformant was obtained. Recombinant plasmid DNA contained in the strain was named pMCE 10. *Escherichia coli* JM 101 strain containing this recombinant plasmid DNA pMCE 10 DNA was cultured in medium composed of 1% (W/V) of tripton, 0.5% (W/V) of yeast extract and 0.5% (W/V) of NaCl at a temperature of 37° C. for 16 to 24 hours. 20 ml of the thus obtained culture solution of *Escherichia coli* JM 101 (pMCE 10) was inoculated on 1 liter of the medium followed by shake culture at a temperature of 37° C. for 3 hours. After the addition of 0.2 g of chloramphenicol, cultivation was conducted at the same temperature for further 20 hours to give a culture solution.

Next, the culture solution was centrifuged at 6,000 r.p.m. for 10 minutes in a conventional manner to give 2 g of wet cells. After the cells were suspended in 20 ml of 350 mM Tris-hydrochloride buffer (pH 8.0) containing 25% (W/V) sucrose, 10 mg of lysozyme, 8 ml of 0.25 M EDTA solution (pH 8.) and 8 ml of 20% (W/V) sodium dodecyl sulfate were added to the suspension, respectively. The mixture was kept at a temperature of 60° C. for 30 minutes to give a lysate solution.

To the lysate solution was added 13 ml of 5 M NaCl solution. The mixture was treated at a temperature of 4° C. for 16 hours and then centrifuged at 15,000 r.p.m. in a conventional manner to give an extract. The extract was subjected to an extraction treatment with phenol and a precipitation treatment with ethanol in a conventional manner to give precipitates.

Then, the precipitates were dried under reduced pressure in a conventional manner and dissolved in 10 mM Tris-hydrochloride buffer (pH 7.5) containing 1 mM EDTA. To the solution were further added 6 g of cesium chloride and 0.2 ml of ethydium bromide solution (10 mg/ml). The resulting mixture was subjected to an equilibrated density gradient centrifugation treatment using a ultracentrifuging machine at 39,000 r.p.m. for 42 hours in a conventional manner thereby to isolate recombinant plasmid pMCE 10 DNA. After ethydium bromide was removed using n-butanol, dialysis was performed to 10 mM Tris-hydrochloride buffer (pH 7.5) containing 1 mM EDTA to 500 μg of purified recombinant plasmid pMCE 10 DNA.

6. Preparation of vector DNA

The thus obtained recombinant plasmid pMCE 10 DNA, 15 μg, was dissolved in 90 μl of TE buffer described in Item 4. After 10 μl of Med buffer [100 mM Tris-hydrochloride buffer (pH 7.5)/10 mM $MgCl_2$/10 mM dithiothreitol/500 mM NaCl] was added to the solution, 30 units of restriction enzyme Acc I (manufactured by Takara Shuzo Co., Ltd.) was further added to the mixture. A cleavage treatment was conducted at a temperature of 37° C. for an hour to give the cleavage product. To the cleavage product was added 100 μl of water-saturated phenol, whereby protein was removed. Then, the aqueous phase was recovered and a 1/10-fold amount of 3 M sodium acetate (pH 7.5) and a 2-fold amount of cold ethanol were added to the aqueous phase. After allowing to stand at a temperature of −70° C. for 15 minutes, the mixture was centrifuged at 12,000 r.p.m. for 10 minutes to recover DNA.

This DNA was dissolved in 10 μl of TE buffer and 15 μl of a mixture [280 mM sodium cacodylate (pH 6.8)/60 mM Tris-hydrochloride buffer (pH 6.8)/2 mM cobalt chloride] was added to the solution. Then, 5 μl of a tailing solution mixture (described in Item 4) (5 mM dGTP was used instead of 5 mM dCTP) was further added to the mixture. Furthermore, 5 units of terminal transferase (manufactured by Takara Shuzo Co., Ltd.) was added to react at a temperature of 37° C. for 15 minutes. By after-treatment in a manner similar to the c-DNA tailing reaction described in Item 4, DNA with the tail of deoxyguanosine at the Acc I site of recombinant plasmid pMCE 10 DNA was prepared.

On the other hand, preparation of DNA with a tail of deoxyguanosine at the Pst I site of plasmid pUC 19 DNA was performed at the same time.

To a solution of 30 μg of plasmid pUC 19 DNA (manufactured by Takara Shuzo Co., Ltd.) in 350 μl of TE buffer were added 40 μl of Med buffer and 120 units of restriction enzyme Pst I (manufactured by Takara Shuzo Co., Ltd.). After a cleavage treatment at a temperature of 37° C. for an hour, DNA was recovered by a treatment of removing protein with phenol and a precipitation treatment with ethanol in a conventional manner.

The obtained DNA was dissolved in 35 μl of TE buffer. To the solution were added 50 μl of a mixture [280 mM sodium cacodylate (pH 6.8)/60 mM Tris-hydrochloride buffer (pH 6.8)/2 mM cobalt chloride], 19 μl of the tailing mixture (containing dGTP instead of dCTP) described in Item 4 and 60 units of terminal transferase (manufactured by Takara Shuzo Co., Ltd.). After reacting at a temperature of 37° C. for 10 minutes, DNA was recovered by a treatment of removing protein with phenol and a precipitation treatment with ethanol in a conventional manner.

7. Annealing and transformation

The synthesized c-DNA, 15 ng and 200 ng of vector DNA were dissolved in 35 μl of annealing buffer [10 mM Tris-hydrochloride buffer (pH 7.5)/100 mM NaCl/1 mM EDTA]. The solution was allowed to stand at a temperature of 65° C. for 2 minutes, at a temperature of 46° C. for 2 hours, at a temperature of 37° C. for an hour and at a temperature of 20° C. for 18 hours thereby to anneal c-DNA and vector DNA.

Using the annealed DNA, *Escherichia coli* DH1 strain (ATCC 33849) was transformed by the method of Hanahan [DNA Cloning, 1, 109–135 (1985)] to prepare c-DNA bank containing plasmid pUC 19 DNA and recombinant plasmid pMCE 10 DNA as vectors, respectively.

8. Survey of luciferase c-DNA

The Acc I site of recombinant plasmid pMCE 10 DNA is present at a site which codes for *Escherichia coli* β-galactosidase gene. Therefore, c-DNA incorporated into this site forms a fused protein with β-galactosidase. Further a promoter of β-galactosidase gene of the recombinant plasmid pMCE 10 DNA has been converted into a promoter of *Escherichia coli* tryptophane gene, as described above.

96 colonies of c-DNA having recombinant plasmid pMCE 10 DNA as a vector were shake cultured in 10 ml of M9 Casamino acid medium [Molecular Cloning, 440–441, Cold Spring Harbor Laboratory (1982)] supplemented with thiamine (10 μg/ml) at a temperature of 37° C. for 10 hours. After collecting the cells in a conventional manner, the cells were suspended in 200 μl of sample buffer for SDS-PAGE described in Item 2. The suspension was boiled at a temperature of 100° C. for 5 minutes.

This suspension, 40 μl, was subjected to electrophoresis in a conventional manner using 7.5% (W/V) polyacrylamide gel. After completion of the electrophoresis, the protein developed on the gel was transferred onto a nitrocellulose filter by the western blot method [Anal. Biochem., 112, 195 (1981)]. This nitrocellulose filter was stained with anti-luciferase serum using immune blot assay kit (manufactured by Biorad Co.). The method was performed in accordance with the operation of Biorad Co.

That is, the nitrocellulose filter was shaken in 100 ml of blocking solution [TBS buffer [20 mM Tris-hydrochloride buffer/500 mM NaCl (pH 7.5)] containing 3% (W/V) gelatin at a temperature of 25° C. for 30 minutes. Next, this nitrocellulose filter was transferred into 25 ml of primary antibody solution [solution obtained by dissolving 1% (W/V) gelatin in TBS buffer and diluting luciferase anti-serum with the resulting solution] and shaken at a temperature of 25° C. for 90 minutes, which was then transferred into 100 ml Tween-20 washing solution [solution obtained by dissolving 0.05% (W/V) Tween-20 in TBS buffer] and shaken at a temperature of 25° C. for 10 minutes. This operation was repeated twice. Then, the thus obtained nitrocellulose filter was transferred into 60 ml of secondary antibody solution [solution obtained by dissolving anti-rabbit antibody labeled with horse raddish peroxidase (manufactured by Biorad Co.) with a solution of 1% (W/V) gelatin in TBS buffer in 3000-fold (V/V). After shaking at a temperature of 25° C. for 60 minutes, the nitrocellulose filter was washed with 100 ml of Tween-20 washing solution. The operation described above was repeated twice. The thus obtained nitrocellulose filter was transferred into 120 ml of color forming solution [solution obtained by mixing a solution of 60 mg of 4-chloro-1-naphthol in 20 ml of cold methanol and a solution of 60 μl of 30% (V/V) hydrogen peroxide aqueous solution in 100 ml of TBS buffer] to form a color at a temperature of 25° C. for 10 minutes.

As such, similar procedures were performed on 4 groups, one being 96 colonies. In two groups, protein band stained with luciferase anti-serum was recognized. Next, 96 colonies belonging to the two groups were divided into 8 groups of 12 colonies each and similar operations were conducted. A protein that reacted with anti-luciferase serum was noted in one group. Finally, with respect to 12 colonies contained in this group, each colony was treated in a similar manner, whereby a protein-producing colony that reacted with luciferase anti-serum was identified. By the foregoing operations, 2 colonies having luciferase c-DNA were obtained. From the two colonies, plasmid DNA was prepared by the method described in Item 5. The obtained recombinant plasmid DNAs were named pALf2B8 and pALf3A6, respectively.

9. Survey of large luciferase c-DNA - Preparation of c-DNA probe

In 330 μl of TE buffer was dissolved 100 μg of recombinant plasmid, pALf3A6 DNA. To the solution were added 40 μl of Low buffer [100 mM Tris-hydrochloride buffer (pH 7.5)/100 mM $MgCl_2$/10 mM dithiothreitol], 130 units of Pst I (manufactured by Takara Shuzo Co., Ltd.) and 120 units of Sac I (manufactured by Boehringer Mannheim Co.) to effect cleavage at a temperature of 37° C. for 1.5 hours.

The whole amount of DNA was separated by electrophoresis using 0.7% (W/V) agarose gel. The agarose gel electrophoresis was carried out in accordance with the method of T. Maniatis et al., Molecular Cloning, pages 156-161, Cold Spring Harbor Laboratory (1984)]. DNA band containing luciferase c-DNA was excised and put in a dialysis tube. After 2 ml of TE buffer was supplemented, the dialysis tube was sealed and DNA was eluted from the gel into the buffer by electrophoresis. An equivalent volume of water-saturated phenol was added to this solution. After agitation, the aqueous phase was recovered and DNA was recovered by precipitation with ethanol in a conventional manner.

10 μg of the obtained DNA fragment was dissolved in TE buffer and 16 μl of Med buffer and 64 units of Sau 3 AI (manufactured by Takara Shuzo Co., Ltd.) were added to the solution. After reacting at a temperature of 37° C. for 2 hours, the whole amount was subjected to electrophoresis using 5% (W/V) polyacrylamide gel thereby to isolate DNA fragments. The polyacrylamide gel electrophoresis was carried out in accordance with the method of A. Maxam [Methods in Enzymology, 65, 506 (1980)]. DNA fragment of 190 bp was isolated by the method as described above to give 1 μg of Sau3 AI luciferase c-DNA fragment.

Using [α-$^{32}$P] dCTP (manufactured by Amersham Co.), 1 μg of this luciferase c-DNA was labeled according to the nick translation method. The nick translation method was performed using a kit manufactured by Takara Shuzo Co., Ltd. in accordance with the method described in J. Mol. Biol., 113, 237-251 (1977) and Molecular Cloning, pages 109-112, Cold Spring Harbor Laboratory (1982).

10. Survey of large luciferase c-DNA - Colony hybridization

Using as a probe the luciferase c-DNA fragment labelled with $^{32}$P prepared by the method described above, c-DNA bank of the tail of *Photinus pyralis* wherein recombinant plasmid pUC 19 DNA was a vector was surveyed by colony hybridization [(Protein, Nucleic Acid and Enzyme, 26, 575-579 (1981)] to give colonies having luciferase c-DNA. Recombinant plasmid DNA possessed by one of the colonies was named pALf3 and plasmid DNA was prepared by the method described in Item 5. *Escherichia coli* containing the recombinant plasmid DNA was named *Escherichia coli* DH 1 (pALf3). The transformant has been deposited as ATCC 67462.

The recombinant plasmid pALf3 DNA described above was subjected to single digestion and double digestion using Xba I, Hind III, BamH I, EcoR I and Pst I (all manufactured by Takara Shuzo Co., Ltd.). The obtained DNA fragments were analyzed by agarose gel electrophoresis on mobility pattern. By comparing the obtained mobility pattern with standard mobility pattern of DNA fragment obtained by digesting λDNA (manufactured by Takara Shuzo Co., Ltd.) with Hind III, the size of the c-DNA inserted in pALf3 was turned out to be 1,700 bp. A restriction enzyme map of the plasmid described above is shown in FIG. 1.

11. Preparation of m-RNA of *Luciola cruciata*

Ten grams of living *Luciola cruciata* (purchased from Seibu Department Store) were put in a ultra-low temperature freezer box and frozen. Each tail was cut off with scissors. To 2 g of the obtained tail was added 18 ml of guanidine isothiocyanate solution. According to the method described in Item 1, 1.1 mg of RNA was prepared. In accordance with the method described in Item 1, 1.1 mg of this RNA was subjected to column chromatography of oligo (dT)-cellulose to prepare 30 μg of *Luciola cruciata* tail m-RNA.

12. Preparation of c-DNA bank of *Luciola cruciata* tail

Synthesis of c-DNA was performed using a kit purchased from Amersham Co. in accordance with the method indicated by Amersham Co. which is described in Mol. Cell Biol., 2, 161 (1982) and Gene, 25, 263 (1983).

From 2 μg of the *Luciola cruciata* tail RNA, 0.9 μg of double stranded c-DNA was synthesized. Using the method described in Item 4, a tail of polydeoxycytidine was added to 0.3 μg of this c-DNA.

This c-DNA, 20 ng, and 500 ng of pUC 19 plasmid prepared in Item 6, wherein a polyguanosine tail had been added to the Pst I site thereof, were annealed in accordance with the method described in Item 7. *Escherichia coli* DH 1 strain (ATCC 3849) was transformed by annealed DNA by the method of Hanahan DNA Cloning, 1, 109-135 (1985)] thereby to prepare c-DNA bank of *Luciola cruciata* tail.

13. Survey of luciferase c-DNA derived from *Luciola cruciata*

In 90 μl of TE buffer was dissolved 10 μg of recombinant plasmid pALf3 DNA and, 10 μl of Med buffer, 25 units of restriction enzyme EcoR I and 25 units of restriction enzyme Cla I (both manufactured by Takara Shuzo Co., Ltd.) were added to the solution. The reaction was performed at a temperature of 37° C. for 2 hours to cleave DNA. From the cleaved recombinant plasmid pALf3 DNA, 800 bp of EcoR I/Cla I DNA fragment containing luciferase c-DNA derived from *Photinus pyralis* (American firefly) was isolated in accordance with the method described in Item 9 using agarose gel electrophoresis. Thus, 1 μg of EcoR I/Cla I DNA fragment was obtained. Using [α-$^{32}$P] dCTP triphosphate (manufactured by Amersham Co.], 1 μg of this DNA was labelled with $^{32}$P in accordance with the nick translation method described in Item 9. Using as a probe the EcoR I/Cla I DNA fragment labeled with $^{32}$P, c-DNA bank of the *Luciola cruciata* tail was surveyed by the colony hybridization described in Item 10 thereby to select *Escherichia coli* having luciferase c-DNA derived from *Luciola cruciata*. Several strains of *Escherichia coli* capable of hybridizing with the probe were obtained. Recombinant plasmid DNA possessed by one of these colonies was named pGLf1. The recombinant plasmid DNA was isolated in accordance with the method described in Item 5. *Escherichia coli* containing the recombinant plasmid DNA was named *Escherichia coli* DH 1 (pGLf1). The transformant has been deposited as ATCC 67482.

Figure 2:
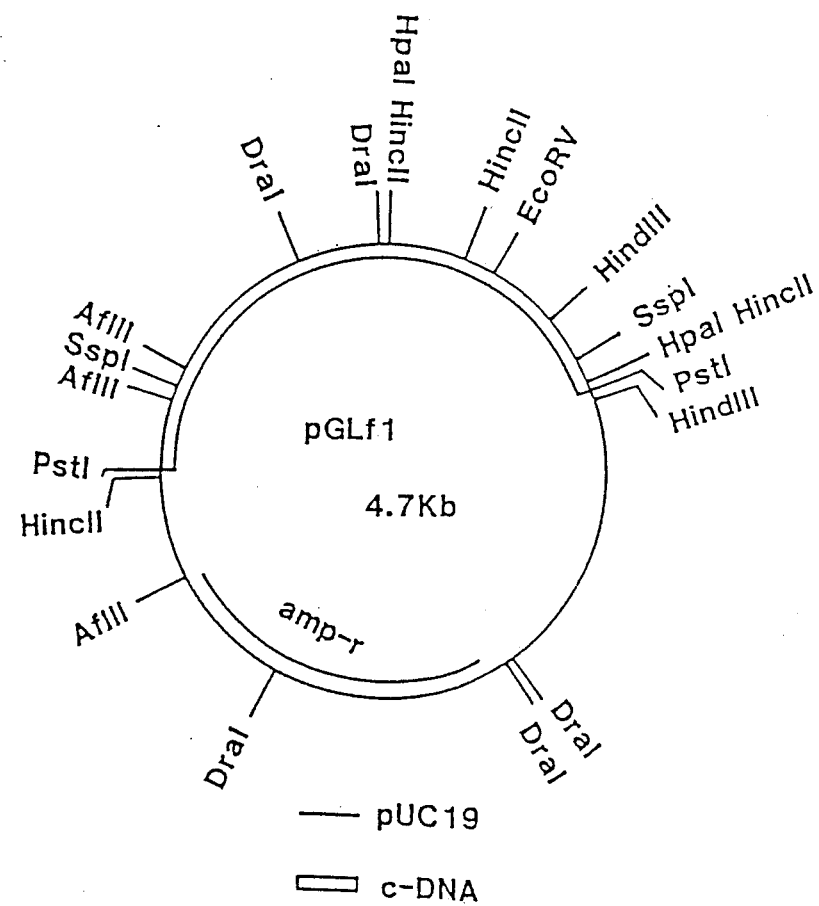
FIG. 2 shows a cleavage map of recombinant plasmid pGLf1 DNA with restriction enzymes.

The recombinant plasmid pGLf1 DNA described above was subjected to single digestion and double digestion using Hpa I, Hind III, EcoR V, Dra I, Afl II, Hinc II, Pst I (all manufactured by Takara Shuzo Co., Ltd.) and Ssp I (manufactured by New England Biolab Co.). The obtained DNA fragments were analyzed by agarose gel electrophoresis on mobility pattern. By comparing the obtained mobility pattern with standard mobility pattern of DNA fragment obtained by digesting λDNA (manufactured by Takara Shuzo Co., Ltd.) with Hind III, the size of the c-DNA inserted in pGLF1 was turned out ot be 2,000 bp. A restriction enzyme map of the plasmid described above is shown in FIG. 2.

14. Analysis of base sequence of luciferase c-DNA derived from *Luciola cruciata*

Recombinant plasmid pGLf1 DNA, 10 μg, was cleaved with restriction enzyme Pst I (manufactured by Takara Shuzo Co., Ltd.) to give 2.5 μg of 2.0 Kb DNA fragment containing luciferase c-DNA. This DNA fragment was cloned at the Pst I site of plasmid pUC 119 DNA (manufactured by Takara Shuzo Co., Ltd.). The obtained plasmid DNAs were named pGLf2 and pGLf3, respectively, depending upon difference in the direction of inserting c-DNA. A cleavage treatment of recombinant plasmid pGLf1 DNA and plasmid pUC 119 DNA with Pst I (method described in Item 6), isolation of the luciferase c-DNA fragments using agarose gel electrophoresis (described in Item 9), ligation of plasmid pUC 119 DNA and luciferase c-DNA fragment (described in Item 5), transformation of *Escherichia coli* JM 101 strain (ATCC 33876) using the ligation reaction solution (described in Item 5) and preparation of recombinant plasmid pGLf2 and pGlf3 DNAs (described in Item 5) followed the methods described within parentheses.

Next, using the recombinant plasmid pGLf2 and pGlf3 DNAs, plasmid DNAs wherein various deletions were introduced into luciferase c-DNA were prepared using a deletion kit for killosequence (manufactured by Takara Shuzo Co., Ltd.) in accordance with the method of Henikoff [Gene, 28, 351–359 (1984)], followed by introducing into *Escherichia coli* JM 101 strain (ATCC 33876) described in Item 5. By infecting the thus obtained *Escherichia coli* with helper phage M13K07 (manufactured by Takara Shuzo Co., Ltd.), single strand DNA was prepared in accordance with the method of Messing [Methods in Enzymology, 101, 20–78 (1983)]. Sequencing with the obtained single strand DNA was carried out by the method of Messing described above, using M13 sequencing kit (manufactured by Takara Shuzo Co., Ltd.). Gel electrophoresis for analyzing a base sequence was carried out using 8% (W/V) polyacrylamide gel (manufactured by Fuji Photo Film Co., Ltd.).

The base sequence of the luciferase-coding region of *Luciola cruciata*-derived luciferase c-DNA alone is shown in FIG. 3. An amino acid sequence of the protein translated from the c-DNA is shown in FIG. 4.

15. Construction of recombinant plasmid pGLf15 DNA

To a solution of 5 μg of recombinant plasmid pGLf1 DNA in 90 μl of TE buffer were added 10 μl of Med buffer and 25 units of Ssp I (manufactured by New England Biolab Co., Ltd.)]. After digesting at a temperature of 37° C. for 2 hours, an equivalent volume of water-saturated phenol was added thereto, whereby operation of removing protein was conducted in a conventional manner. From the digested recombinant plasmid pGLf15 DNA, 1.6 Kb DNA fragment coding for *Luciola cruciata*-derived luciferase c-DNA was isolated by utilizing the method using agarose gel electrophoresis described in Item 9. Thus, 1 μg of 1.6 Kb Ssp I fragment was obtained.

On the other hand, 1 μg of plasmid pUC 18 DNA (manufactured by Takara Shuzo Co., Ltd.) was dissolved in 18 μl of TE buffer and, 2 μl of Sma I buffer [100 mM Tris-hydrochloride buffer (pH 8.0)/70 mM magnesium chloride/200 mM potassium chloride/70 mM 2-mercaptoethanol/0.1% bovine serum albumin] and 5 units of Sma I (manufactured by Takara Shuzo Co., Ltd.) were added to the solution. After digesting at a temperature of 37° C. for an hour, extraction with phenol and precipitation with ethanol were performed in a conventional manner to give precipitates.

In 7 μl of water were dissolved 0.5 μg of the Sma I-digested plasmid pUC 18 DNA and 0.5 μg of 1.6 Kb *Luciola cruciata*-derived luciferase c-DNA fragment. To the solution was added 13 μl of a mixture [77 mM Tris-hydrochloride buffer (pH 7.4)/15 mM magnesium chloride/15 mM dithiothreitol/0.15 mM adenosine triphosphate] and 1 unit of T4 ligase (manufactured by Boehringer Mannheim AG). The mixture was subjected to ligation at a temperature of 8° C. for 18 hours. Using the reaction solution, *Escherichia coli* JM 101 strain (ATCC 33876) was transformed as described in Item 7. From the obtained transformants, plasmid DNA was isolated as described in Item 5. The isolated plasmid DNA was subjected to single digestion with Hind III (manufactured by Takara Shuzo Co., Ltd.) and a plasmid DNA forming 1.5 Kb and 2.9 Kb DNA fragments was selected. This recombinant plasmid DNA was named pGLf15 and *Escherichia coli* bearing this plasmid DNA was named *Escherichia coli* JM 101 (pGLf15). *Escherichia coli* JM 101 (pGLf15) has been deposited as ATCC 67461.

*Escherichia coli* JM 101 (pGLf15) was cultured by the method described in Item 5. By isolating the recombinant plasmid DNA, 1.2 mg of purified recombinant pGLf15 DNA was obtained from 1 liter of the culture solution.

16. Cultivation of *Escherichia coli* JM 101 (pGLf15) (ATCC 67461) and preparation of crude enzyme solution

*Escherichia coli* JM 101 (pGLf15) (ATCC 67461) was shake cultured in 3 ml of LB-amp medium [1% (W/V) bactotripton, 0.5% (W/V) yeast extract, 0.5% (W/V) NaCl and ampicillin (50 μg/ml)] at a temperature of 37° C. for 18 hours. This culture solution, 0.5 ml, was inoculated on 10 ml of the aforesaid LB-amp medium and 1 mM isopropyl-β-D-thiogalactoside was added thereto. After shake culture at a temperature of 37° C. for 4 hours, the culture was subjected to a centrifuging operation at 8,000 r.p.m. for 10 minutes to give 20 mg of wet cells.

The recovered cells were suspended in 0.9 ml of buffer composed of 0.1 M $KH_2PO_4$ (pH 7.8), 2 mM EDTA, 1 mM dithiothreitol and 0.2 mg/ml protamine sulfate. Further 100 μl of 10 mg/ml lysozyme solution was supplemented to the suspension. The mixture was allowed to stand in ice for 15 minutes. Next, the suspension was frozen in methanol-dry ice bath and then allowed to stand at a temperature of 25° C. to completely freeze. Further by performing a centrifuging operation at 12,000 r.p.m. for 5 minutes, 1 ml of crude enzyme solution was obtained as the supernatant.

The luciferase activity in the thus obtained crude enzyme solution was performed by the method described below. The results are shown in the table below.

The measurement of luciferase activity in the crude enzyme solution obtained was performed by counting the number of photon formed in accordance with the method of Kricka [Archives of Biochemistry and Biophysics, 217, 674 (1982)].

That is, 260 μl of 25 mM glycylglycine buffer (pH 7.8), 16 μl of 0.1 M magnesium sulfate and 24 μl of 1 mM luciferine (manufactured by Sigma Co.) and 10 μl of the crude enzyme solution were mixed. Then 100 μl of 20 mM ATP was added to the mixture. The number of photon formed was integrated for 20 seconds. The integrated values were shown in the table below.

For purpose of comparison, luciferase activity was measured also with *Escherichia coli* JM 101 strain bearing plasmid pUC 18 DNA [*Escherichia coli* JM 101 (pUC 18)]. The results are shown in the table below.

TABLE

| Sample | Item Number of Photon/ml Culture Solution |
|---|---|
| *Escherichia coli* | $8.3 \times 10^6$ |

TABLE-continued

| Sample | Item Number of Photon/ml Culture Solution |
|---|---|
| JM 101 (pGLf15) (invention) | |
| *Escherichia coli* JM 101 (pUC 18) (control) | $9.8 \times 10^4$ |

As is clear from the table above, it is noted that the count of photon increased in the present invention as compared to the comparison and therefore, luciferase is produced in the cells of *Escherichia coli* used in the present invention.

While the invention has been described in detail and with reference to specific embodiments thereof, it is apparent to one skilled in the art that various changes and modifications can be made therein without departing from the spirit and the scope of the present invention.

What is claimed is:

1. An isolated luciferase gene coding for an amino acid sequence shown in FIG. 4.

2. An isolated luciferase gene according to claim 1, having a DNA sequence of FIG. 3.

3. A recombinant DNA comprising an isolated luciferase DNA from *Luciola cruciata*.

4. A recombinant DNA according to claim 3 wherein said isolated luciferase DNA has a nucleotide sequence shown in FIG. 3.

5. A recombinant DNA according to claim 3 wherein said isolated luciferase DNA codes for an amino acid sequence of FIG. 4.

6. A recombinant DNA according to claim 3, wherein said isolated luciferase DNA from *Luciola cruciata* is inserted into plasmid pUC18 DNA.

7. A method of producing luciferase which comprises culturing, in a medium, a microorganism belonging to the genus Escherichia capable of producing luciferase, said microorganism containing a recombinant DNA having inserted therein an isolated luciferase gene from *Luciola cruciata* and collecting luciferase from the culture.

8. A method of producing luciferase according to claim 7, wherein said gene codes for an amino acid sequence shown in FIG. 4.

9. A method of producing luciferase according to claim 7 wherein said gene has a nucleotide sequence shown in FIG. 3.

10. A method for producing luciferase according to claim 7, wherein said recombinant DNA is one produced by inserting an isolated luciferase gene from *Luciola cruciata* into pUC18 DNA.

* * * * *